(12) United States Patent
Lenhard et al.

(10) Patent No.: US 8,871,441 B2
(45) Date of Patent: Oct. 28, 2014

(54) MICROFLUIDIC DEVICE SCREENING METHOD

(75) Inventors: Thomas Lenhard, Kgs. Lyngby (DK); Mads Eskelund Bjoernvad, Virum (DK); Poul Erik Pedersen, Farum (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 13/059,454

(22) PCT Filed: Aug. 14, 2009

(86) PCT No.: PCT/EP2009/060542
§ 371 (c)(1),
(2), (4) Date: Feb. 17, 2011

(87) PCT Pub. No.: WO2010/020589
PCT Pub. Date: Feb. 25, 2010

(65) Prior Publication Data
US 2011/0159511 A1    Jun. 30, 2011

Related U.S. Application Data

(60) Provisional application No. 61/090,930, filed on Aug. 22, 2008.

(30) Foreign Application Priority Data

Aug. 21, 2008  (EP) .................................... 08162761

(51) Int. Cl.
| | | |
|---|---|---|
| *C12Q 1/68* | (2006.01) | |
| *C12Q 1/02* | (2006.01) | |
| *C12Q 1/533* | (2006.01) | |
| *C12N 1/21* | (2006.01) | |

(52) U.S. Cl.
CPC .............. *C12Q 1/02* (2013.01); *G01N 2333/99* (2013.01); *C12Q 1/533* (2013.01)
USPC ....................................... 435/6.1; 435/252.31

(58) Field of Classification Search
None
See application file for complete search history.

(56) References Cited

U.S. PATENT DOCUMENTS 5,024,943 A * 6/1991 Van Ee .......................... 435/6.18
5,916,796 A * 6/1999 Jørgensen et al. ............ 510/321
2006/0135457 A1   6/2006 Paterson

FOREIGN PATENT DOCUMENTS

| WO | WO 2007-081385 A2 | 7/2007 |
|---|---|---|
| WO | WO 2007-081386 A2 | 7/2007 |
| WO | WO 2007-081387 A1 | 7/2007 |
| WO | WO 2007-133710 A2 | 11/2007 |
| WO | WO 2008-063227 A2 | 5/2008 |

OTHER PUBLICATIONS

Easley et al., Proc. Natl. Acad. Sci. USA, 103 (51) 19272-19277, 1006.*
Vehmaanpera, FEMS Microbiol., Lett., 61:165-170, 1989.*
Pragai et al., Microbiology, 140:305-310, 1994.*
Pierce et al., FEMS Microbiol. Lett. 283:69-74, 2008.*
Diderichsen, "A Genetic System for Stabilization of Cloned Genes in *Bacillus subtilis*", *Bacillus* Molecular Genetics and Biotechnology Applications, Novo Res Institute DK, pp. 35-46 (1986).
Ferrari et al., "Isolation of an Alanine Racemase Gene from *Bacillus subtilis* and its use for Plasmid Maintenance in *B. Subtilis*", Bio/Technology, vol. 3, pp. 1003-1007 (1985).
Huang et al., "Recent advances in single-cell analysis using capillary electrophoresis and microfluidic devices", Journal of Chromatography, vol. 866, pp. 104-122 (2008).
Pierce et al., "Gene cloning and characterization of a second alanine racemase from *Bacillus subtilis* encoded *byyncD*", FEMS Microbiology Letters, vol. 283, pp. 69-74 (2008).
Shilling, "Basic Microfluidic Concepts", pp. 1-8 Internet Article (2001).
Tauch et al., "The alanine racemase gene *alr* is an alternative to antibiotic resistance genes in cloning systems for industrial *Corynebacterium glutamicum* strains", Journal of Biotechnology, vol. 99, No. 1, pp. 79-91 (2002).
Xia et al., "Construction of an integrative food-grade expression system for *Bacillus subtilis*", Food Research International, vol. 38, No. 3, pp. 251-256 (2005).

* cited by examiner

*Primary Examiner* — Nancy T Vogel
(74) *Attorney, Agent, or Firm* — Elias Lambiris

(57) ABSTRACT

The invention provides methods of screening a microbial host cell for a property of interest in a microfluidic device, the method comprising the steps of: a) transforming a d-alanine racemase-deficient microbial host cell with a polynucleotide construct comprising: i) one or more polynucleotide region providing the property of interest when present in the host cell, and ii) at least one polynucleotide region complementing the d-alanine racemase deficiency when present in the host cell; and b) screening the transformed host cell for the property of interest in the microfluidic device in the absence of externally provided d-alanine.

17 Claims, 2 Drawing Sheets dal region in DN1686
4045 bp dal region in HeHe004
5226 bp comS-dcat MiBg601
9761 bp HeHe004 alr-10R
15674 bp

MICROFLUIDIC DEVICE SCREENING METHOD

CROSS-REFERENCE TO RELATED APPLICATIONS

This application is a 35 U.S.C. 371 national application of PCT/EP2009/060542 filed Aug. 14, 2009, which claims priority or the benefit under 35 U.S.C. 119 of European application no. 08162761.4 filed Aug. 21, 2008 and U.S. provisional application No. 61/090,930 filed Aug. 22, 2008, the contents of which are fully incorporated herein by reference.

FIELD OF THE INVENTION

The present invention relates to methods of screening a microbial host cell for a property of interest in a microfluidic device, the method comprising the steps of:
   a) transforming a d-alanine racemase-deficient microbial host cell with a polynucleotide construct comprising:
      i) one or more polynucleotide region providing the property of interest when present in the host cell, and
      ii) at least one polynucleotide region complementing the d-alanine racemase deficiency when present in the host cell; and
   b) screening the transformed host cell for the property of interest in the microfluidic device in the absence of externally provided d-alanine.

BACKGROUND OF THE INVENTION

Microfluidics technology, i.e. nanoliter to picoliter size droplets on or in disposable chips for biochemical analysis, is becoming increasingly prevalent as networks of small channels have been proven to be a flexible platform for the precision manipulation of such small amounts of fluids.

One way of handling microfluidic reagents is by producing aqueous droplets in an immiscible, inert carrier fluid as disclosed in WO 2007081385, WO 2007081386, WO 2007081387, WO 2007133710 and WO 2008063227 (Raindance Technologies Inc). These suspended droplets provide a well defined, encapsulated microenvironment that eliminates cross contamination and allows for sequential cycling of reagents. They can be used to isolate reactive materials, cells, proteins, or small particles for further manipulation and study, and droplets containing specific properties can be selectively removed from the droplet population and collected.

For microbiological applications using cellular expression of proteins, droplets can be sized to contain a cell and at the same time minimize the extracellular volume, resulting in high extracellular concentrations of protein and hence, rapid and sensitive assays. These droplets can be used for enrichment of library elements that can be subjected to secondary mining to optimize a broad range of protein characteristics. Ultra-high throughput screening combines the use of pre-screening techniques and computational search methods to maximize library analysis, resulting in the exploration of a very large protein sequence-space.

The manufacture and use of microfluidic devices is well-known as is their use to screen chemical libraries, e.g., comprising polynucleotides, which after microfluidic screening and/or sorting are transformed into a host cell for expression.

In routine *Bacillus subtilis* transformation procedures, only about 1 in 10,000 cells are actually transformed. Generally, an antibiotic resistance gene is provided together with a gene of interest which prevents untransformed cells from growing in the presence of an added antibiotic. Even though untransformed cells are not able to grow or divide under antibiotic stress, they will usually survive being exposed to the commonly used antibiotics and resume growth once the antibiotic is removed. In fact, many commonly used antibiotics are not really true antibiotics in the sense that they do not kill the cells; most so-called antibiotics would be termed more accurately bacteriostatics.

Due to the relatively low transformation efficiency, a gene library has to be 50,000-fold overscreened to compensate for the total variant dilution. This adds on top of the redundancy of a diversity library, that in itself has to be 5-fold overscreened to cover the diversity.

In theory, nano- to pico-size droplet microfluidics technology allows the screening of as much as 1000 cells per second. However, in real applications this number is reduced by the fact that the cells are diluted during droplet packaging, so that only about 1 in 5 droplet contains a cell. This is done to increase the likelihood, that the droplets contain a maximum of 1 cell when inoculated. A consequence is that an unmanageably large number of cells have to screened in order to cover an entire gene library.

A way to increase the rate of transformed vs. untransformed cells in transformations of microorganisms would be to use a selection principle, whereby the untransformed cells are actually killed, preferably without the need to add anything to the growth medium. Such an improvement of transformation efficiency would be of particular relevance in microfluidic applications.

SUMMARY OF THE INVENTION

D-alanine is a compound of the cell wall of many microorganisms, including *Bacillus* species; it is synthesized in the cell by an enzyme, d-alanine racemase. Genes coding for d-alanine racemase are well-known in many species and genera (see below). It has been shown earlier in *Bacillus subtilis* DN1686, a derivative containing a chromosomal deletion in the d-alanine racemase encoding gene, that truncation of the gene results in d-alanine racemase deficiency. Such cells grown in liquid medium or on agar plates without d-alanine are not able to survive, they rapidly lyse and die unless supplemented with d-alanine.

The combination of using d-alanine racemase deficient host cells together with d-alanine free growth medium and a transformation polynucleotide construct that complements the deficiency, provides a neat way to dramatically improve the efficiency of a microfluidic screening method without the need to use antibiotics.

The present invention reduces the ratio of transformanted vs. non-transformanted microbial cells to as little as 1:2, which means that up to 3,300 times fewer cells will have to be screened, thus making it feasible to employ direct screening of transformed microbial cells in a microfluidic setup.

This ingenious combination even allows in situ microfluidic transformation of highly competent host cells thus obviating the usual pre-screening transformation protocol.

Accordingly, in a first aspect, the present invention provides a method of screening a microbial host cell for a property of interest in a microfluidic device, the method comprising the steps of:
   a) transforming a d-alanine racemase-deficient microbial host cell with a polynucleotide construct comprising:
      i) one or more polynucleotide region providing the property of interest when present in the host cell, and ii) at least one polynucleotide region complementing the d-alanine racemase deficiency when present in the host cell; and b) screening the transformed host cell for the property of interest in the microfluidic device in the absence of externally provided d-alanine.

A second aspect of the invention relates to the use of a d-alanine racemase-deficient microbial host cell in a microfluidic device screening method for a property of interest.

DETAILED DESCRIPTION OF THE INVENTION

Figure 1:
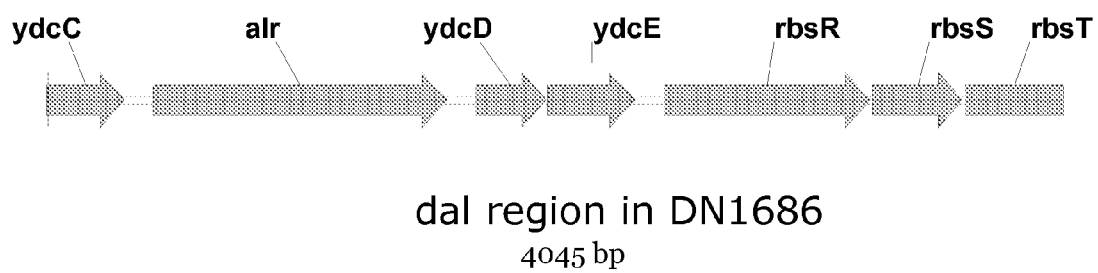
FIG. 1 shows a schematic of the 4054 basepair *Bacillus subtilis* DN1686 alr-locus.

The first aspect of the invention relates to a method of screening a microbial host cell for a property of interest in a microfluidic device, the method comprising the steps of:

a) transforming a d-alanine racemase-deficient microbial host cell with a polynucleotide construct comprising:
   i) one or more polynucleotide region providing the property of interest when present in the host cell, and
   ii) at least one polynucleotide region complementing the d-alanine racemase deficiency when present in the host cell; and
b) screening the transformed host cell for the property of interest in the microfluidic device in the absence of externally provided d-alanine.

Microfluidic Device

The microfluidic devices and methods of use described herein are based on the creation and electrical manipulation of aqueous phase droplets completely encapsulated by an inert fluorocarbon oil stream. This combination enables electrically addressable droplet generation, highly efficient droplet coalescence, precision droplet breaking and recharging, and controllable single droplet sorting. Additional passive modules include multi-stream droplet formulations, mixing modules, and precision break-up modules. The integration of these modules is an essential enabling technology for a droplet based, high-throughput microfluidic reactor system.

Microfluidic devices can use a flow-focusing geometry to form the droplets. For example, a water stream can be infused from one channel through a narrow constriction; counter propagating oil streams (preferably fluorinated oil) hydrodynamically focus the water stream and stabilize its breakup into micron size droplets as it passes through the constriction. In order to form droplets, the viscous forces applied by the oil to the water stream must overcome the water surface tension. The generation rate, spacing and size of the water droplets is controlled by the relative flow rates of the oil and the water streams and nozzle geometry. While this emulsification technology is extremely robust, droplet size and rate are tightly coupled to the fluid flow rates and channel dimensions. Moreover, the timing and phase of the droplet production cannot be controlled. To overcome these limitations, the microfluidic devices of the present invention can incorporate integrated electric fields, thereby creating an electrically addressable emulsification system hi one embodiment, this can be achieved by applying high voltage to the aqueous stream and charge the oil water interface. The water stream behaves as a conductor while the oil is an insulator; electrochemical reactions charge the fluid interface like a capacitor. At snap-off, charge on the interface remains on the droplet. The droplet size decreases with increasing field strength. At low applied voltages the electric field has a negligible effect, and droplet formation is driven exclusively by the competition between surface tension and viscous flow, as described above.

The microfluidic, droplet-based reaction-confinement system can further include a mixer which combines two or more reagents to initiate a chemical reaction. Multi-component droplets can easily be generated by bringing together streams of materials at the point where droplets are made. However, all but the simplest reactions require multiple steps where new reagents are added during each step. In droplet-based microfluidic devices, this can be best accomplished by combining (i.e. coalescing) different droplets, each containing individual reactants. However, this is particularly difficult to achieve in a microfluidic device because surface tension, surfactant stabilization, and drainage forces all hinder droplet coalescence; moreover, the droplets must cross the stream lines that define their respective flows and must be perfectly synchronized to arrive at a precise location for coalescence. The microfluidic devices of the present invention overcome these difficulties by making use of electrostatic charge, placing charges of opposite sign on each droplet, and applying an electric field to force them to coalesce.

The electrodes used to charge the droplets upon formation also provide the electric field to force the droplets across the stream lines, leading to coalescence. In the absence of an electric field, droplets in the two streams do not in general arrive at the point of confluence at exactly the same time. When they do arrive synchronously the oil layer separating the droplets cannot drain quickly enough to facilitate coalescence and as a result the droplets do not coalesce. In contrast, upon application of an electric field, droplet formation becomes exactly synchronized, ensuring that droplets each reach the point of confluence simultaneously (i.e., paired droplets).

Moreover, since the droplets are oppositely charged they are attracted to one another, which forces them to traverse the fluid stream lines and contact each other, thereby causing them to coalesce. The synchronization of the droplet formation results from coupling of the break-off of each of the pair of droplets as mediated by the electric field. The use of oppositely charged droplets and an electric field to combine and mix reagents is extremely robust, and 100% of the droplets coalesce with their partner from the opposite stream.

The microfluidic devices can also include a droplet sorter. The contents of individual droplets must be probed, and selected droplets sorted into discreet streams. In one embodiment, such sorting in microfluidic devices can be accomplished through the use of mechanical valves. The use of electrostatic charging of droplets provides an alternate means of sorting that can be precisely controlled, can be switched at high frequencies, and requires no moving parts. Electrostatic charge on the droplets enables drop-by-drop sorting based on the linear coupling of charge to an external electric field. As an example, a T-junction bifurcation that splits the flow of carrier fluid equally will also randomly split the droplet population equally into the two streams. However, a small electric field applied at the bifurcation precisely dictates which channel the drops enter. Varying the direction of the field varies the direction of the sorted droplets. The large forces that can be imparted on the droplets and the short time required to switch the field make this a fast and robust sorting engine with no moving parts; thus the processing rate is limited only by the rate of droplet generation and electric field switching time, and can easily exceed 20,000 per second.

An "analysis unit" is a microfabricated substrate, e.g., a microfabricated chip, having at least one inlet channel, at least one main channel, at least one coalescence module, and at least one detection module. The analysis unit can further contain one or more sorting module. The sorting module can be in fluid communication with branch channels in communication with one or more outlet modules (collection module or waste module). For sorting, at least one detection module cooperates with at least one sorting module to divert flow via a detector-originated signal. It shall be appreciated that the "modules" and "channels" are in fluid communication with each other and therefore may overlap; i.e., there may be no clear boundary where a module or channel begins or ends. A device according to the invention may comprise a plurality of analysis units.

A variety of channels for sample flow and mixing can be microfabricated on a single chip and can be positioned at any location on the chip as the detection or sorting modules, e.g., for kinetic studies. A plurality of analysis units of the invention may be combined in one device. Microfabrication applied according to the invention eliminates the dead time occurring in conventional gel electrophoresis or flow cytometric kinetic studies, and achieves a better time-resolution. Furthermore, linear arrays of channels on a single chip, i.e., a multiplex system, can simultaneously detect and sort a sample by using an array of photo multiplier tubes (PMT) for parallel analysis of different channels. This arrangement can be used to improve throughput or for successive sample enrichment, and can be adapted to provide a very high throughput to the microfluidic devices that exceeds the capacity permitted by conventional flow sorters. Circulation systems can be used in cooperation with these and other features of the invention. Positive displacement pressure driven flow is a preferred way of controlling fluid flow and electric fields and electric field gradients are a preferred way of manipulating droplets within that flow.

Microfabrication permits other technologies to be integrated or combined with flow cytometry on a single chip, such as PCR, moving cells using optical tweezer/cell trapping, transformation of cells by electroporation, μTAS, and DNA hybridization. Detectors and/or light filters that are used to detect cellular characteristics of the reporters can also be fabricated directly on the chip. Preferably, detectors are off-chip free space optics or off-chip electronics with on-chip leads.

A "channel," as used herein, means a feature on or in a device (e.g., a substrate) that at least partially directs the flow of a fluid, hi some cases, the channel may be formed, at least in part, by a single component, e.g., an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet. A channel may have an aspect ratio (length to average cross-sectional dimension) of at least 2:1, more typically at least 3:1, 5:1, or 10:1. As used herein, a "cross-sectional dimension," in reference to a fluidic or microfluidic channel, is measured in a direction generally perpendicular to fluid flow within the channel. An open channel generally will include characteristics that facilitate control over fluid transport, e.g., structural characteristics (an elongated indentation) and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus), hi an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 ran, or less than about 10 nm or less in some cases. In one embodiment, the channel is a capillary. Of course, in some cases, larger channels, tubes, etc. can be used to store fluids in bulk and/or deliver a fluid to the channel. In some embodiments, the dimensions of the channel may be chosen such that fluid is able to freely flow through the channel, for example, if the fluid contains cells. The dimensions of the channel may also be chosen, for example, to allow a certain volumetric or linear flow rate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, etc.

A "main channel" is a channel of the device of the invention which permits the flow of molecules, cells, small molecules or particles past a coalescence module for coalescing one or more droplets, a detection module for detection (identification) or measurement or a droplet and a sorting module, if present, for sorting a droplet based on the detection in the detection module. The coalescence, detection and/or sorting modules can be placed or fabricated into the main channel. The main channel is typically in fluid communication with an inlet channel or inlet module. An "inlet channel" permits the flow of molecules, cells, small molecules or particles into the main channel. One or more inlet channels communicate with one or more means for introducing a sample into the device of the present invention.

The inlet channel communicates with the main channel at an inlet module. The main channel is also typically in fluid communication with an outlet module and optionally with branch channels, each of which may have a collection module or waste module. These channels permit the flow of cells out of the main channel.

A microfluidic device can include a bifurcation geometry designed in such a manner as to minimize fluidic shear forces on droplets during sorting. Known devices describe bifurcation geometries in which significant shear forces affect droplets during sorting. Specifically droplets may experience shear forces when moving under the influence of the sorting force across the width of the input channel prior to encountering the bifurcation, and droplets may experience shear forces at the bifurcation point which are applied in such a manner as to elongate or even tear the droplet apart.

A microfluidic device comprising channels having a bifurcation geometry can minimize these shear forces by (i) including a necked-down segment of the input channel upstream of the bifurcation where the droplet is diagnosed to make the sorting decision, and/or by (ii) including a flaired-out segment of the input channel immediately prior to the bifurcation, and/or by (iii) including a fork on the far wall of the bifurcation. The shear forces are minimized by component (i) because the sorting field is applied while the droplet is in the necked-down segment. Therefore, when the droplet exits the necked-down segment, the droplet is placed on fluid streamlines, which will carry it out the desired branch of the bifurcation. Furthermore, the droplet does not significantly encounter fluid streamlines, which follow the undesired branch of the bifurcation. The shear forces are minimized by component (ii) because the droplet does not significantly impact the far wall of the bifurcation at a point where it would experience fluid streamlines, which follow the undesired branch of the bifurcation. The shear forces are minimized by component (iii) because the fork serves to focus the two sets of fluid streamlines (i.e., the one set which follows one branch of the bifurcation, and the other set which follows the other branch of the bifurcation) away from each other.

A microfluidic device can include a specific geometry designed in such a manner as to prevent the aggregation of biological/chemical material and keep the biological/chemical material separated from each other prior to encapsulation in droplets. The geometry of channel dimension can be changed to disturb the aggregates and break them apart by various methods, that can include, but is not limited to, geometric pinching (to force cells through a (or a series of) narrow region(s), whose dimension is smaller or comparable to the dimension of a single cell) or a barricade (place a series of barricades on the way of the moving cells to disturb the movement and break up the aggregates of cells).

Channel design can force biological/chemical material moving along the center streamline through flow focus, e.g., using two dilution channels at the entrance of the channel to prevent attachment to the channel surface. This can also be used to prevent the surface attachment by cells. Droplets at these dimensions tend to conform to the size and shape of the channels, while maintaining their respective volumes. Thus, as droplets move from a wider channel to a narrower channel they become longer and thinner, and vice versa. Droplets can be at least about four times as long as they are wide. This droplet configuration, which can be envisioned as a lozenge shape, flows smoothly and well through the channels. Longer droplets, produced in narrower channels, provides a higher shear, meaning that droplets can more easily be sheared or broken off from a flow, i.e. using less force. Droplets can also tend to adhere to channel surfaces, which can slow or block the flow, or produce turbulence. Droplet adherence is overcome when the droplet is massive enough in relation to the channel size to break free. Thus, droplets of varying size, if present, can combine to form uniform droplets having a so-called critical mass or volume that results in smooth or laminar droplet flow. Droplets that are longer than they are wide, preferably about four times longer than they are wide, generally have the ability to overcome channel adherence and move freely through the microfluidic device. Thus, in an exemplary embodiment with 60 micron channels, a typical free-flowing droplet is about 60 microns wide and 240 microns long. Droplet dimensions and flow characteristics can be influenced as desired, in part by changing the channel dimensions, e.g. the channel width.

The term "emulsion" refers to a preparation of one liquid distributed in small globules (also referred to herein as drops, droplets or NanoReactors) in the body of a second liquid. The first and second fluids are immiscible with each other. For example, the discontinuous phase can be an aqueous solution and the continuous phase can a hydrophobic fluid such as an oil. This is termed a water in oil emulsion. Alternatively, the emulsion may be a oil in water emulsion, hi that example, the first liquid, which is dispersed in globules, is referred to as the discontinuous phase, whereas the second liquid is referred to as the continuous phase or the dispersion medium. The continuous phase can be an aqueous solution and the discontinuous phase is a hydrophobic fluid, such as an oil (e.g., decane, tetradecane, or hexadecane). The droplets or globules of oil in an oil in water emulsion are also referred to herein as "micelles", whereas globules of water in a water in oil emulsion may be referred to as "reverse micelles".

As used herein, the term "NanoReactor" and its plural encompass the terms "droplet", "microdrop" or "microdroplet" as defined herein, as well as an integrated system for the manipulation and probing of droplets, as described in detail herein. Nanoreactors as described herein can be 0-100 μm (e.g., 5, 10, 15, 20, 25, 30, 35, 40, 45, 50, 55, 60, 65, 70, 75, 80, 85, 90, 95, 100) The droplet forming liquid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer.

Any liquid or buffer that is physiologically compatible with the population of molecules, cells or particles to be analyzed and/or sorted can be used. The fluid passing through the main channel and in which the droplets are formed is one that is immiscible with the droplet forming fluid. The fluid passing through the main channel can be a non-polar solvent, most preferably decane (e.g., tetradecane or hexadecane), fluorocarbon oil or another oil (for example, mineral oil).

The dispersed phase fluid may also contain biological/chemical material (e.g., molecules, cells, or other particles) for combination, analysis and/or sorting in the device. The droplets of the dispersed phase fluid can contain more than one particle or can contain no more than one particle. For example, where the biological material comprises cells, each droplet preferably contains, on average, no more than one cell. The droplets can be detected and/or sorted according to their contents.

The fluids used in the invention may contain one or more additives, such as agents which reduce surface tensions (surfactants). Surfactants can include Tween, Span, fluorosurfactants, and other agents that are soluble in oil relative to water. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

The droplets may be coated with a surfactant. Preferred surfactants that may be added to the continuous phase fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglycerl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates). In addition, ionic surfactants such as sodium dodecyl sulfate (SDS) may also be used. However, such surfactants are generally less preferably for many embodiments of the invention. For instance, in those embodiments where aqueous droplets are used as nanoreactors for chemical reactions (including biochemical reactions) or are used to analyze and/or sort biomaterials, a water soluble surfactant such as SDS may denature or inactivate the contents of the droplet.

The carrier fluid can be an oil (e.g., decane, tetradecane or hexadecane) or fluorocarbon oil that contains a surfactant (e.g., a non-ionic surfactant such as a Span surfactant) as an additive (preferably between about 0.2 and 5% by volume, more preferably about 2%). A user can preferably cause the carrier fluid to flow through channels of the microfluidic device so that the surfactant in the carrier fluid coats the channel walls.

In one embodiment, the fluorosurfactant can be prepared by reacting the perflourinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Flourinert (3M)), which then serves as the continuous phase of the emulsion.

The invention can use pressure drive flow control, e.g., utilizing valves and pumps, to manipulate the flow of cells, particles, molecules, enzymes or reagents in one or more directions and/or into one or more channels of a microfluidic device. However, other methods may also be used, alone or in combination with pumps and valves, such as electro-osmotic flow control, electrophoresis and dielectrophoresis (Fulwyer, Science 156, 910 (1974); Li and Harrison, Analytical Chemistry 69, 1564 (1997); Fiedler, et al. Analytical Chemistry 70, 1909-1915 (1998); U.S. Pat. No. 5,656,155). Application of these techniques according to the invention provides more rapid and accurate devices and methods for analysis or sorting, for example, because the sorting occurs at or in a sorting module that can be placed at or immediately after a detection module. This provides a shorter distance for molecules or cells to travel, they can move more rapidly and with less turbulence, and can more readily be moved, examined, and sorted in single file, i.e., one at a time.

Details of the manufacture and use of microfluidic devices of the invention are readily available from WO 2007081385, WO 2007081386, WO 2007081387, WO 2007133710 and WO 2008063227 (Raindance Technologies Inc).

Host Cell

The term "microbial host cell", as used herein, includes any cell type that is susceptible to transformation, transfection, transduction, and the like with a nucleic acid construct or expression vector A vector or construct comprising a polynucleotide providing an activity of interest, e.g. one or more gene encoding an enzymatic activity, is introduced into a host cell so that the vector is maintained as a chromosomal integrant or as a self-replicating extra-chromosomal vector. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis*, and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus*, and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E.*

*coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

As mentioned in the above, d-alanine is a compound of the cell wall of many microorganisms, including *Bacillus* species; it is synthesized in the cell by an enzyme, d-alanine racemase. The gene coding for d-alanine racemase (UNIPROT:P10725) in *Bacillus subtilis* is alr (alanine racemase); another term used for the same gene is dal (d-alanine racemase) (Ferrari, E. et al. 1985. Isolation of an alanine racemase gene from *Bacillus subtilis* and its use for plasmid maintenance in *B. subtilis*. Biotech 3:1003-1007).

It has been shown earlier in *Bacillus subtilis* DN1686, a derivative containing a chromosomal deletion in the alr gene, that truncation of the gene results in d-alanine racemase deficiency. Such cells grown in liquid medium or on agar plates without d-alanine are not able to survive, they rapidly lyse and die unless supplemented with d-alanine. However, a polynucleotide encoding an active d-alanine racemase transformed into an alr-knockout strain is able to complement the deficiency (Diderichsen B, 1986, A genetic system for stabilization of cloned genes in *Bacillus subtilis*. *Bacillus* Molecular Genetics and Biotechnology Applications, pp. 35-46).

Recently it was disclosed that *Bacillus subtilis* besides alr comprises a second d-alanine racemase (UNIPROT:P94494) encoding gene, yncD, which is not normally expressed, but which under certain circumstances may become constitutively expressed and thereby allow growth of otherwise d-alanine racemase deficient cells. A comparison of the amino acid sequences of a number of d-alanine racemases was provided from *Mycobacterium avium, Corynebacterium glutamicum, Lactobacillus plantarum, Bacillus stearothermophilus* and *Bacillus subtilis*. In addition, a comprehensive phylogenetic analysis revealed that the Gram-positive enzymes (Dal and YncD) are evolutionarily distinct from the Gram-negative enzymes (Alr and DadX), even though they complement each other in vivo, and that the Dal and YncD proteins from different species of *Bacillus* clearly cluster together in divergent groups on the Gram-positive side of the tree (see FIG. 3 of Pierce K J et al., 2008, Gene cloning and characterization of a second alanine racemase from *Bacillus subtilis* encoded by yncD. FEMS Microbiol Lett 283 pp. 69-74).

Accordingly, in a preferred embodiment of the invention, the d-alanine deficient host cell carries at least one mutation in one or more chromosomal gene encoding a d-alanine racemase, whereby the gene is silenced or the encoded d-alanine racemase is inactivated; preferably, the at least one mutation comprises an insertion, a deletion or a substitution of at least one nucleotide; and most preferably, the at least one mutation comprises a truncation of the gene.

Polynucleotide Construct

The present invention also relates to nucleic acid or polynucleotide constructs comprising an isolated polynucleotide providing a property of interest when present in the host cell, typically the polynucleotide encodes a polypeptide having a property of interest, which polynucleotide is operably linked to one or more (several) control sequences that direct the expression of a coding sequence in a suitable host cell under conditions compatible with the control sequences.

An isolated polynucleotide encoding a polypeptide of interest may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid construct, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (VIIIa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), *Bacillus clausii* alcaline protease (aprH) and *Bacillus subtilis* prsA. Further signal peptides are described by Simonen and Palva, 1993, *Microbiological Reviews* 57: 109-137.

The control sequence may also be a propeptide coding sequence that codes for an amino acid sequence positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, xyl and trp operator systems.

In a preferred embodiment of the polynucleotide construct in the first aspect of the invention, the one or more polynucleotide region providing the property of interest comprises a genomic, variant or cDNA library.

In another preferred embodiment of the invention, the property of interest is an enzymatic activity; preferably the enzymatic activity is encoded by the one or more polynucleotide region of step i); more preferably, the enzymatic activity is a lyase, a ligase, a hydrolase, an oxidoreductase, a transferase, or an isomerase; or most preferably, the enzymatic activity is an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinase, peroxidase, phytase, phenoloxidase, polyphenoloxidase, protease, ribonuclease, transferase, transglutaminase, or a xylanase.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by nonhomologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

EXAMPLES

Example 1

Truncation of alr in *Bacillus subtilis*

For the construction, we introduced a gene encoding antibiotic resistance for tetracycline into the alr-locus of *Bacillus subtilis* DN1686 by homologous recombination, resulting in a d-alanine racemase deficient strain. Thereby, 94 bp of the alr-gene has been replaced. The alr-locus of *Bacillus subtilis* DN1686 is shown in FIG. 1.

Figure 2:
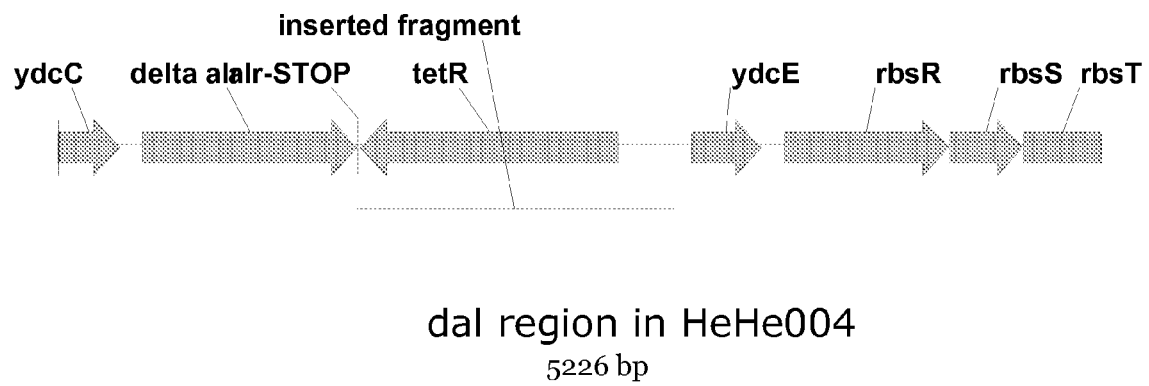
FIG. 2 shows a schematic of the 5226 basepair alr deletion construct.

A PCR product featuring the deletion construct shown in FIG. 2 was transformed into *Bacillus subtilis* MiBg-601 (a DN1686 derivate) resulting in tet-resistant transformants, which were selected on LB agar plates containing 10 microgram/ml tetracycline and 50 microgram/ml d-alanine. The transformants were not able to grow on LBagar-plates without d-alanine. One resulting cell was selected and denoted HeHe004.

Example 2

Introduction of an Expression Cassette and comS

Figure 3:
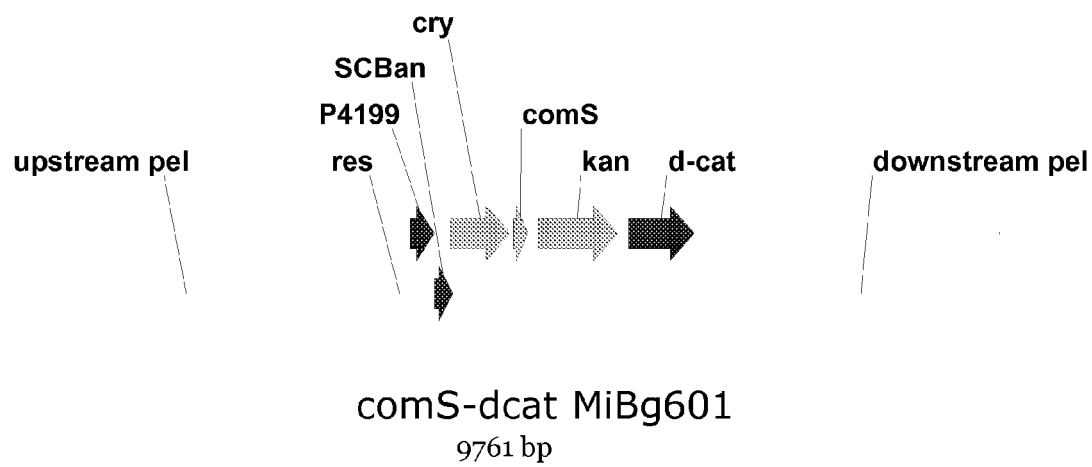
FIG. 3 shows a schematic of a 9761 basepair compentence construct; the pel-locus of *Bacillus subtilis* was used to introduce a cassette for heterologous expression. The comS-gene, driven by the strong CryIIIa-promoter, and a kanamycin-resistance was introduced into the pel-locus, securing highly competent cells and providing a selectable marker. In addition, the cassette features the C-terminal part of the chloramphenicol-resistance gene and regions for homologous cross-over.

A cassette for heterologous polypeptide expression was introduced into the pel-locus of *Bacillus subtilis* HeHe004 by double homologous recombination. The cassette comprises the comS gene driven by the strong CryIIIa-promoter, which provides highly competent cells, a kanamycin-resistance selectable marker, the C-terminal part of the chloramphenicol-resistance gene as well as up- and down-stream pel-regions suitable for homologous recombination. A schematic overview of the resulting genome is shown in FIG. 3.

Example 3

Transformation of a Gene of Interest

Figure 4:
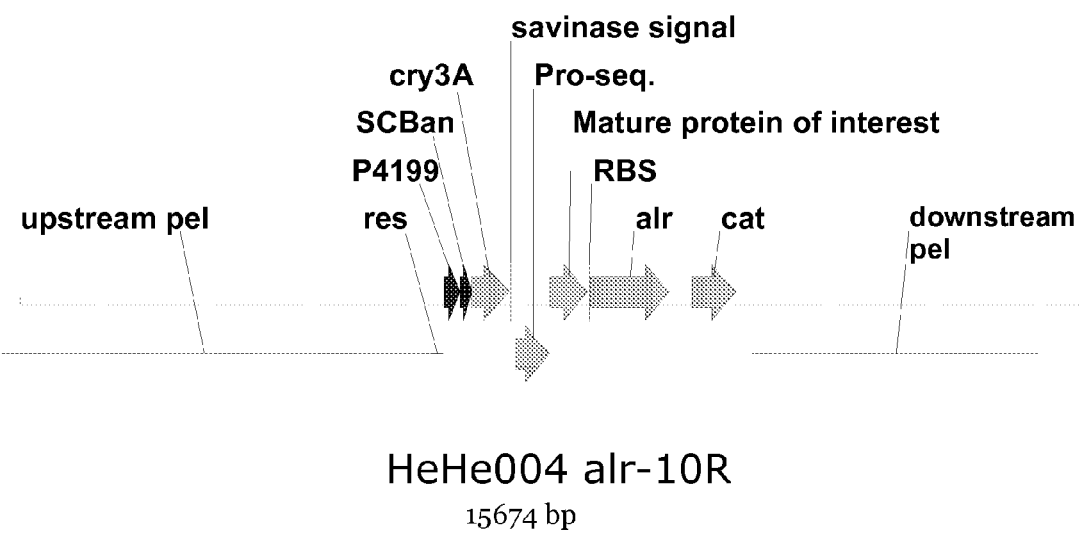
FIG. 4 shows a schematic of the final genomic layout, where transformed DNA comprising the alr ORF has been inserted into the pel locus along with other components, thus compensating for the alr-deficiency.

The highly competent and kanamycine resistant cells of the previous example were transformed with a polynucleotide construct engineered to replace the comS kanamycin cassette with an intact alr-gene and a complete chloramphenicol-gene. A schematic overview of the construct is shown in FIG. 4. The alr-gene is expressed co-transcriptionally together with the gene of interest, which encodes the so-called 10R protease. Transformants were Alr-positive, chloramphenical-resistant and they were able to degrade casein in plates due to 10R protease activity.

Example 3

Complementation of d-Alanine Racemase Deficiency

After the transformation in example 3 we obtained $6*10^4$ primary transformants. The total number of transformed cells was $3*10^8$, which translates to a ratio of 1 transformed cell for every 5,000 untransformed cells.

After incubation of the transformation mixture for about 6 hours in a medium without d-alanine, the ratio of transformed vs. untransformed cells had increased to as much as 1:2. At the same time, each transformed cell had undergone a few replications, thus increasing the redundancy of the library.

A ratio of transformed vs. untransformed cells of 1:2 can easily be handled in a nanodroplet screening method, so d-alanine deficiency complementation is a highly suitable selection principle for nanodroplet screening.

The invention claimed is:

1. A method of screening a *Bacillus* host cell for a property of interest in a microfluidic device, the method comprising the steps of:
   (a) transforming a d-alanine racemase-deficient *Bacillus* host cell with a polynucleotide construct comprising:
      (i) one or more polynucleotide region(s) providing the property of interest when present in the host cell, and
      (ii) at least one polynucleotide region complementing the d-alanine racemase deficiency when present in the host cell; and
   (b) screening the transformed host cell for the property of interest in the microfluidic device in the absence of externally provided d-alanine.

2. The method of claim 1, wherein the *Bacillus* cell is chosen from the group consisting of *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*.

3. The method of claim 1, wherein the one or more polynucleotide region(s) providing the property of interest comprises a genomic, variant or cDNA library.

4. The method of claim 1, wherein the property of interest is an enzymatic activity.

5. The method of claim 4, wherein the enzymatic activity is encoded by the one or more polynucleotide region of step (i).

6. The method of claim 4, wherein the enzymatic activity is a lyase, a ligase, a hydrolase, an oxidoreductase, a transferase, or an isomerase.

7. The method of claim 6, wherein the enzymatic activity is an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinase, peroxidase, phytase, phenoloxidase, polyphenoloxidase, protease, ribonuclease, transferase, transglutaminase, or a xylanase.

8. The method of claim 1, wherein the *Bacillus* host cell carries at least one mutation in one or more chromosomal gene(s) encoding a d-alanine racemase, whereby the gene is silenced or the encoded d-alanine racemase is inactivated.

9. The method of claim 8, wherein the at least one mutation comprises an insertion, a deletion or a substitution of at least one nucleotide.

10. The method of claim 9, wherein the at least one mutation comprises a truncation of the gene.

11. The method of claim 1, wherein the *Bacillus* host cell carries at least one mutation in the alr gene, whereby the gene is silenced or the encoded d-alanine racemase is inactivated.

12. The method of claim 9, wherein the *Bacillus* host cell further carries at least one mutation in the yncD gene, whereby the gene is silenced or the encoded d-alanine racemase is inactivated.

13. The method of claim 1, wherein the *Bacillus* cell is a *Bacillus subtilis* cell.

14. The method of claim 1, wherein the *Bacillus* cell is a *Bacillus licheniformis* cell.

15. The method of claim 1, wherein the *Bacillus* cell is a *Bacillus amyloliquefaciens* cell.

16. The method of claim 1, wherein the transformed cell of step (a) is present in a medium having a ratio of transformed cells to untransformed cells of at least 1:5000.

17. The method of claim 1, wherein the transformed cell of step (a) is present in a medium having a ratio of transformed cells to untransformed cells of at least 1:2.

* * * * *